United States Patent [19]

Temple

[11] Patent Number: 5,356,400
[45] Date of Patent: Oct. 18, 1994

[54] LARGE BORE DRAINAGE APPARATUS

[76] Inventor: John E. Temple, 2442 McKinley, Chelsea, Mich. 48118

[21] Appl. No.: 58,487

[22] Filed: May 6, 1993

[51] Int. Cl.$^5$ ............................................. A61B 19/00
[52] U.S. Cl. .................................... 604/356; 604/327
[58] Field of Search ............... 604/322, 326, 327, 277, 604/278, 332, 345, 356, 129; 4/480; 5/600, 604–608

[56] References Cited

U.S. PATENT DOCUMENTS

| | | | |
|---|---|---|---|
| 3,861,396 | 1/1975 | Vaillancourt et al. | 604/129 |
| 4,368,733 | 1/1983 | Sanidas | 604/327 |
| 5,074,850 | 12/1991 | Chion | 604/322 |

FOREIGN PATENT DOCUMENTS 0108736  5/1984  European Pat. Off. ............ 604/327

Primary Examiner—Randall L. Green
Assistant Examiner—Rob Clarke
Attorney, Agent, or Firm—Krass & Young

[57] ABSTRACT

An apparatus for draining a biological substance from a collection bag attached to a patient. The apparatus includes a large bore, thin walled drainage tube which expands to have a substantially circular cross-sectional configuration when a biological substance such as fecal material passes therethrough, and collapses into a substantially flat cross-sectional configuration when the tube is empty. A connector in the form of two adhesively coated, resilient, fluid impervious pieces of sheet material is used to connect the large bore drainage tube to the collection bag.

15 Claims, 2 Drawing Sheets

_5,356,400_

LARGE BORE DRAINAGE APPARATUS

FIELD OF THE INVENTION

This invention concerns the field of collection bags for draining biological fluid from a medical or veterinary patient and, more particularly, of an apparatus for draining such a collection bag.

DESCRIPTION OF THE RELEVANT PRIOR ART

There are many medical and veterinary situations where a biological substance, such as blood, urine, feces, serum, etc. is drained and collected from the body of a patient as the substance is being produced. For example, it is known to attach a fluid catheter to the urinary tract for subsequent attachment to a fluid collection bag. See for example, U.S. Pat. No. 4,619,648. It is also known to attach devices such as colostomy bags and fecal incontinence devices to natural or surgically created orifices of the patient's body for collection of the feces which is produced. See, for example, my U.S. Pat. No. 4,850,986 and patents referenced therein, for a description of a fecal incontinence device.

Typical substance collection bags make it possible for a patient to stay clean and dry even when the patient is comatose or otherwise indisposed. In some cases, the biological substance so collected is simply disposed of, whereas, in other cases, the substance will be at least temporarily preserved for subsequent analysis, such as weighing, measuring, or chemical analysis.

Of course, with any type of bag for a collecting biological substance produced by a patient, the collection bag will eventually become full and the question of how to empty it will arise. This problem is more difficult than it might appear at first blush since removal of the collection bag, particularly those such as a colostomy bag or a fecal incontinence bag, which are attached directly to the patient, can be quite difficult, and subsequent reattachment will be required. Of course, it could be possible to provide the bags with an outlet drain for connection to a larger storage receptacle.

However, such a scheme is difficult to accomplish when anything other than a fairly liquid biological substance is involved. In particular, devices such as colostomy and ostomy appliances, as well as fecal incontinence bags, often collect at least partially semi-solid fecal material. Thus, if such devices are provided with a drainage outlet, the conduit between the outlet and a larger storage receptacle must necessarily be of relatively large bore to accomplish the passage of the semi-solid fecal substance therethrough.

However, prior art attempts to use large bore tubing as a drainage conduit has caused problems in the long term care of fecally incontinent and surgical patients. Large bore PVC tubing typically is formed of a relatively thick gauge of polymer and is quite stiff. Yet, due to the location of the fecal collection appliances on the patient's body, the patient is likely to find such large bore, stiff tubing extremely uncomfortable, particularly if it is encountered in the groin or buttock area. Even if the tubing is used in a more abdominal location, twisting and turning by the patient can result in the patient at least partially lying on the stiff tubing. Hence, when such draining tubing is used with bedridden patients, it is not unusual for rashes, bed sores, and actual tissue fissures to develop which are not only extremely uncomfortable, but represent a medical threat to the well being of the patient.

In an attempt to circumvent this problem, attendants charged with the care of such patients, such as enterostomal therapists, have been known to rig up a connection between a fecal collection appliance and an improvised retention vessel, such as a gallon milk jug, by using a length of accordion pleated flex tubing. However, while more flexible and yielding than the typical large bore, thick walled PVC tubing, even the flex tubing is stiff and unyielding enough to cause problems. Furthermore, such an improvised conduit is difficult to attach to the collection bag, and may result in leakage from a failed connection. Of course, any connection used between the conduit and the collection bag must also be soft and yielding or else it, too, will cause discomfort and the conditions noted above.

Clearly, there is a need for an apparatus for draining collection bags used to accumulate biological substances produced by a medical or veterinary patient. In particular, there is a need for such a drainage device which will allow the passage of solid or semi-solid material therethrough. Furthermore, there is a need for a drainage device which will accommodate other than purely liquid material, yet which is comfortable enough for the patient to lie on or otherwise interact with, and which will not cause rashes, bed sores, tissue fissures, or other undesirable medical conditions.

SUMMARY OF THE INVENTION

Disclosed and claimed herein is an apparatus for draining a biological substance from a collection bag attached to a medical or veterinary patient who is producing such a substance. The apparatus comprises a thin walled, large bore drainage tube which expands to have a substantially circular cross-sectional configuration when the biological substance is passing therethrough and, yet, collapses into a substantially flat cross sectional configuration when the substance is not passing therethrough. The tube is normally in the collapsed, flat configuration. The apparatus further comprises a connector for attaching a first end of the tube to an outlet of the collection bag. In one embodiment of the connector, it comprises two flat, mating pieces of polymeric sheet material having a width somewhat larger than the width of the drainage tube when the tube is in the collapsed configuration. Disposed on the inside surfaces of both mating pieces of the connector is a layer of contact adhesive material. The mating pieces of the connector are supplied with one or more pull off paper strips covering each adhesive layer, preferably with a pull tab formed thereon. When the drainage tube is attached to the outlet of the collection bag, the opposed pieces of the connector are placed on either side of the connection to enclose the overlapping ends of the outlet and the drainage tube. By pulling away the paper strips, the mating adhesive strips are exposed so that they will adhere to the collection bag outlet and drainage tube, as well as to each other. Hence, a fluid tight seal is easily formed. A similar connector can be provided to a second end of the drainage tube for connection to the larger retention vessel. Preferably, the drainage tube is formed of a flexible, polymeric sheet material such as natural latex rubber, silicon, polyvinyl chloride and polyvinyl chloride (PVC) copolymers.

In an alternate embodiment of the apparatus of the present invention, the drain tube may further comprise portions of greater wall thickness formed at opposed ends of the tubing (when in the flat configuration) in order to prevent the tube from twisting while in use.

BRIEF DESCRIPTION OF THE DRAWINGS

The following detailed description may best be understood by reference to the following drawings in which.

DETAILED DESCRIPTION OF THE PREFERRED EMBODIMENTS

Figure 1:
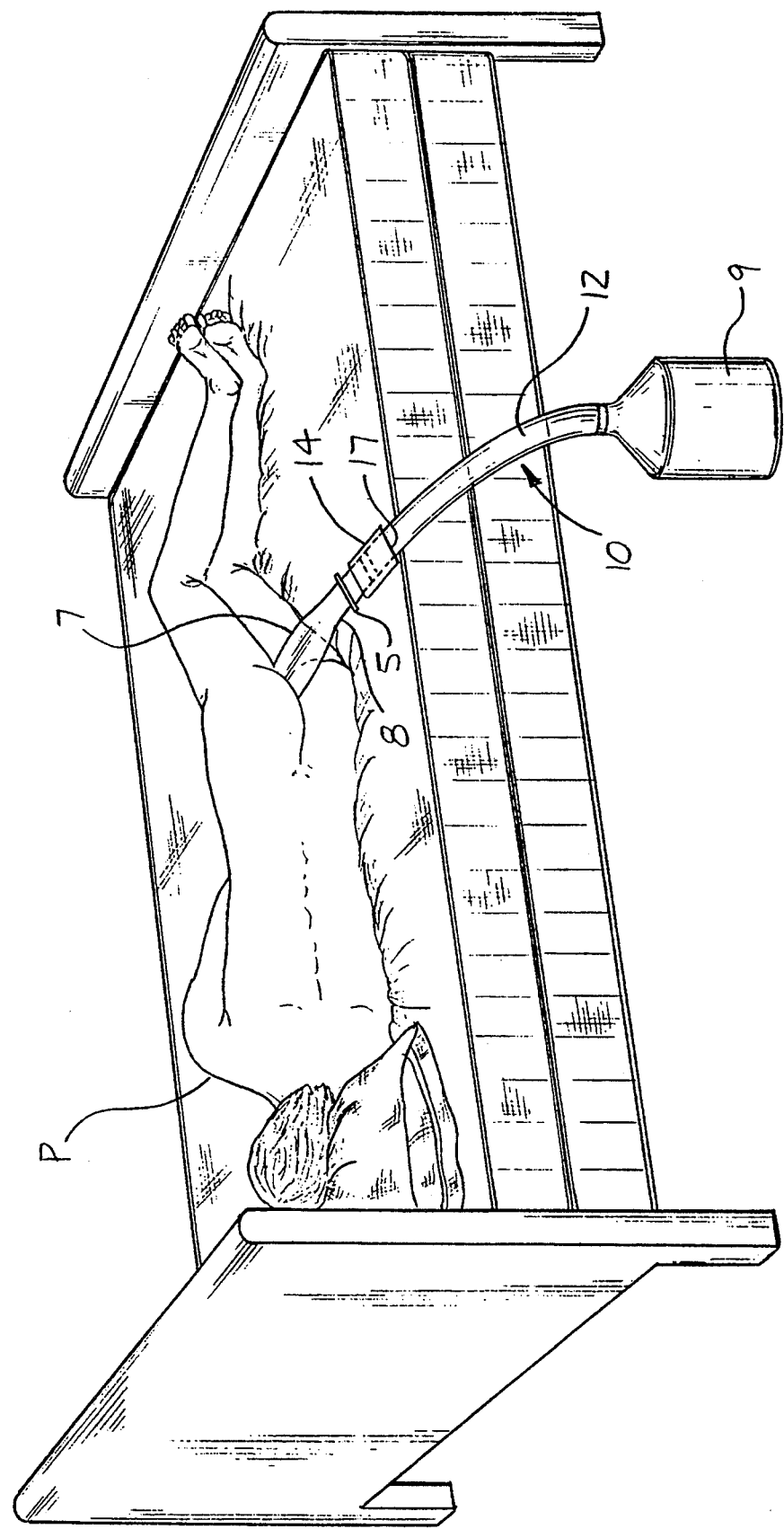
FIG. 1 is a perspective view of the apparatus according to the present invention in use to drain a fecal incontinence bag.

Throughout the following detailed description, like numerals are used to reference the same element of the herein invention shown in multiple figures thereof. Referring now to the drawings, and in particular to FIG. 1, there is depicted an apparatus 10 for draining a biological substance from a collection bag 7 attached to a patient P. In this case, the collection bag is a fecal incontinence device of the type shown in, for example, U.S. Pat. Nos. 4,445,898 or 4,850,986. The fecal incontinence device 7 attaches to the anal area of the patient P and receives feces produced thereby. The bag 7 has an outlet 8 which may be narrower in diameter than the bag 7, or may simply be an open ended continuation of the bag 7.

The apparatus 10 for draining the bag 7 includes a thin walled, large bore drainage tube 12. Typically, the drainage tube 12 is formed of a soft, resilient, easily formed material, such as polyvinyl chloride and polyvinyl chloride copolymers, natural latex rubber, silicon rubber, etc. In order to avoid odor problems caused by the passage of feces through the drainage tube, the wall 13 of the tube 12 must be thick enough. On the other hand, the wall 13 cannot be too thick or it will not collapse properly when empty. Preferably the wall 13 of the tube 12 should have a thickness in a range of approximately 0.015 to 0.040 inches. The large bore drainage tube 12 may be extruded, or it may be formed of a flat piece of sheet material which is RF welded or heat sealed at the edges to form a tube. Typically, the large bore drainage tube 12 has a diameter of approximately two inches to allow the easy passage of semi-solid material therethrough without blockage.

Figure 2:
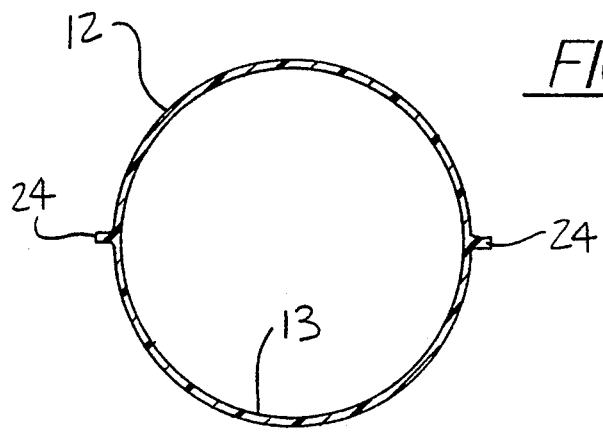
FIG. 2 is a cross-section of the drainage tube of the apparatus of FIG. 1 shown in the expanded configuration.
Figure 3:
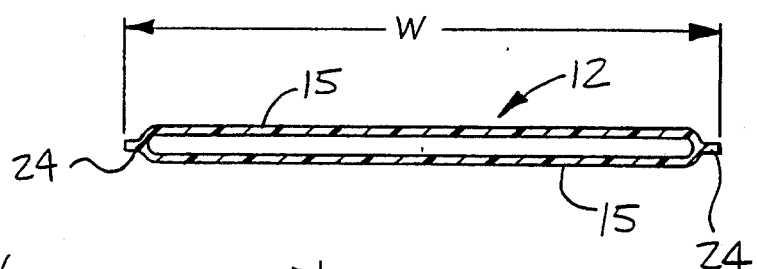
FIG. 3 is similar to FIG. 2 except that the cross-section shows the drain tube in the collapsed configuration.

As can be seen by comparing FIGS. 2 and 3, the large bore drainage tube 12 has a substantially circular configuration when it is in its expanded condition, that is, when material is passing therethrough. However, when material is not passing therethrough, the tube 12 will have the collapsed configuration shown in FIG. 3, with two flat, opposed side walls 15 and two small ends 24. In the embodiment shown in FIG. 3, the small ends 24 have a wall thickness considerably greater than the wall thickness of the remainder of the tube, with their corners rounded. The purpose of these thickened ends 24 is to help prevent twisting of the tube 12 while the patient is moving.

Figure 4:
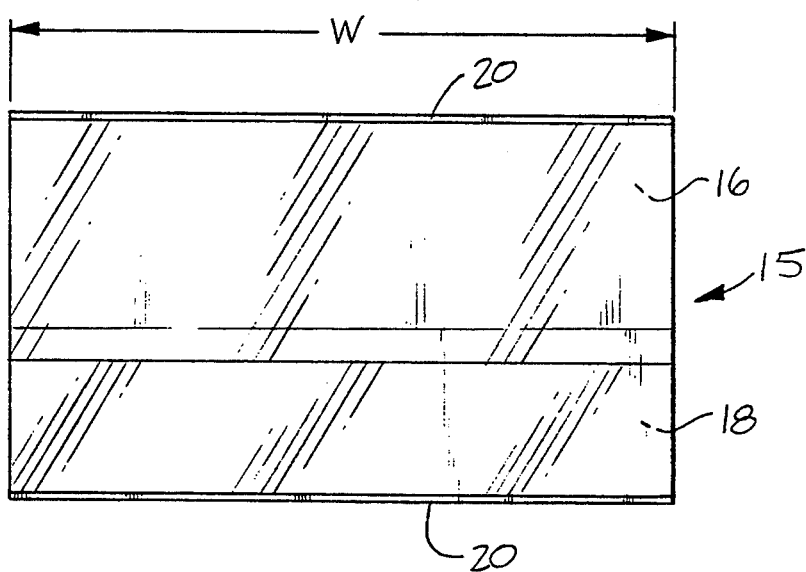
FIG. 4 is a top view of one of the mating connector pieces used to form the connector shown in FIG. 1.
Figure 5:
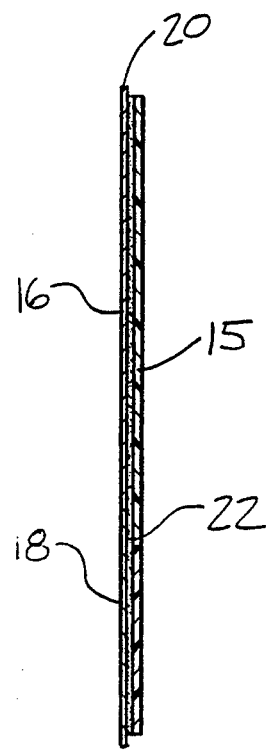
FIG. 5 is an end-on view of the connector piece of FIG. 4.

The drainage tube 12 is attached to the outlet 8 of the bag 7 with a connector 14. As can be seen from the phantom lines shown in FIG. 1, the tube 12 is attached to the outlet 8 so that the ends thereof overlap. The connector 14 is comprised of two opposed, flat pieces 15 of a flexible, fluid impervious material. One of the opposed pieces 15 of which the connector 14 is comprised is shown in greater detail in FIGS. 4 and 5. FIG. 4 is a top view of the connector piece 15, and FIG. 5 is an end-on view thereof. Each connector piece 15 has a width W which is somewhat greater than the diameter w of the drainage tube 12 when in its collapsed configuration. As can be seen in FIG. 1, the greater width W of the connector pieces 15 results in portions 17 of the connector 16 which extend beyond the environs of the bag outlet 8 and the drainage tube 12.

As can best be seen in FIG. 5, each connector piece 15 has a layer 22 of a contact adhesive disposed thereon. In turn, the contact adhesive layer 22 is covered by two strips 16, 18 of peel off paper. The strips 16, 18 each include an extending tab 20 so that the paper may be more easily grasped and peeled off the adhesive layer 22. The connector pieces 15 may be formed of similar materials as the large bore drainage tube 12 so that the connector 16 will not interfere with the expansion and contraction of the drainage tube 12 described above. However, in order to insure a secure seal, the connector 16 typically will be formed of a somewhat thicker sheet material having a wall thickness of at least 0.060 inches. The contact adhesive layer 22 is formed by depositing a layer of a solvent bond adhesive that will adhere on contact to form a secure bond.

The large bore drainage tube 12 is connected to the outlet 8 of the fecal incontinence bag 7 in the following manner. First, the tube 12 is fitted onto the outlet 8 such that the ends thereof overlap. The peel strips 16, 18 are then removed from one of the opposed connector pieces 15 to expose the adhesive layer 22. The piece 15 is then placed over one side of the connection between the outlet 8 and the tube 12 such that the length of the connector spans the overlapping ends, and the width W of the connector piece 15 spans the width w of the drainage tube 12 so as to leave the portions 17 extending on either side. In this way, a single sized connector can be used on different sizes of drainage bags. The peel strips 16, 18 are then removed from the other one of the opposed pair of connector pieces 15, and that piece 15 is fitted on the other side of the connection between the tube 12 and the outlet 8 so that the two connector pieces 15 are in approximate alignment. Pressure is then applied to the opposed connector pieces 15 to form a secure, fluid tight bond between the pieces 15 and portions of the outlet 8 and the tube 12. Of course, the extending portions 17 of the connector pieces 15 will adhere to each other, thus helping to ensure a fluid proof connection between the bag 7 and the drain tube 12. However, by use of a carefully selected solvent bond adhesive, the bond between the various elements will not be so tight that it cannot be broken by carefully unpeeling the connector pieces 15, if this is desired.

The other end 19 of the tube 12 is placed in fluid communication with a larger retention vessel 9. Typically, the outlet 8 of bag 7 will be temporarily closed by such means as clip 5, and the waste material will accumulate in the bag 7. When the bag 7 becomes full, the clip 5 is removed from outlet 8 to allow the waste material to pass through the drain tube 12 and into retention vessel 9 where it may be stored for subsequent disposal or analysis.

The invention disclosed herein has been described with reference to certain embodiments and exemplifications thereof. Doubtless, one skilled in the art, by referring to the teachings of the present specification, may devise other design variations of the present invention. However, such design variations are considered to come within the scope of the present invention which is not limited to those embodiments and exemplifications present herein, but solely by the claims appended hereto and all reasonable equivalents thereof.

I claim:

1. An apparatus for draining a biological substance from a collection bag attached to a patient producing said substance, said apparatus comprising:
   a large bore, thin walled drainage tube which expands to have a substantially circular cross-sectional configuration when a biological substance is passing therethrough and collapses into a substantially flat cross-sectional configuration when said tube is empty, said tube normally being in said collapsed configuration; and
   a flat connector for attaching an end of said tube to an outlet of a collection bag containing said biological substance, said connector comprising two opposed, mating pieces formed of a resilient, fluid impervious material, each of said mating pieces having a width greater than the outside diameter of said drainage tube when said drainage tube is in said collapsed condition such that edge portions of said connector members extend beyond said tube when said connector member is attached to said tube, said connector members further including an adhesive layer disposed thereon for adhesive attachment to said tube end and said drainage bag outlet.

2. The apparatus of claim 1 wherein each connector member further includes at least one paper pull strip disposed on said adhesive layer.

3. The apparatus of claim 2 wherein said least one paper pull strip includes a pull tab extension formed on an edge thereof.

4. The apparatus of claim 1 wherein said large bore drainage tube has a wall thickness between 0.015 and 0.040 inches.

5. The apparatus of claim 1 wherein said drainage tube is formed of polyvinyl chloride.

6. The apparatus of claim 1 wherein said drainage tube has a second end in fluid communication with a storage receptacle to receive said biological substance.

7. The apparatus of claim 1 wherein said biological substance is at least partially solid or semi-solid in form.

8. The apparatus of claim 1 wherein each connector member further includes at least one paper pull strip disposed on said adhesive layer.

9. The apparatus of claim 8 wherein said least one paper pull strip includes a pull tab extension formed on an edge thereof.

10. An apparatus for draining a biological substance from a collection bag attached to a patient producing said substance, said apparatus comprising:
    a large bore, thin walled drainage tube which expands to have a substantially circular cross-sectional configuration when a biological substance is passing therethrough and collapses into a substantially flat cross-sectional configuration when said tube is empty, said tube normally being in said collapsed configuration, said drainage tube having a rectangular cross section when collapsed and including two flat, opposed sides and two rounded, opposed ends, each of said ends having a wall thickness substantially thicker than a wall thickness of said opposed sides to prevent twisting of said tube when in use; and
    a connector for attaching an end of said tube to a collection bag containing said biological substance, said connector comprising two opposed, mating pieces formed of a resilient, fluid impervious material, each of said mating pieces having a width greater than the outside diameter of said drainage tube when said drainage tube is in said collapsed condition such that edge portions of said connector members extend beyond said tube when said connector member is attached to said tube, said connector members further including an adhesive layer disposed thereon.

11. An apparatus for draining a fecal incontinence bag attached to a patient, said apparatus comprising:
    a large bore, thin walled drainage tube which expands to have a substantially circular cross-sectional configuration when fecal material is passing therethrough and collapses into a substantially flat cross-sectional configuration when said tube is empty, said tube normally being in said collapsed configuration; and
    a flat connector for attaching an end of said tube to an outlet of a fecal incontinence bag containing said fecal material, said connector comprising two opposed, mating pieces formed of a resilient, fluid impervious material, each of said mating pieces having a width greater than the outside diameter of said drainage tube when said drainage tube is in said collapsed condition such that edge portions of said connector members extend beyond said tube when said connector member is attached to said tube, said connector members further including an adhesive layer disposed thereon for adhesive attachment to said tube end and said drainage bag outlet.

12. The apparatus of claim 11 wherein said large bore drainage tube has a wall thickness between 0.015 and 0.040 inches.

13. The apparatus of claim 11 wherein said drainage tube is formed of polyvinyl chloride.

14. The apparatus of claim 11 wherein said drainage tube has a second end in fluid communication with a storage receptacle to receive said fecal material.

15. The apparatus of claim 11 wherein said outlet of said fecal incontinence bag is formed by an open end of said bag.

* * * * *